United States Patent
Shemesh et al.

(10) Patent No.: US 7,847,267 B2
(45) Date of Patent: Dec. 7, 2010

(54) SCANNING ELECTRON MICROSCOPE HAVING MULTIPLE DETECTORS AND A METHOD FOR MULTIPLE DETECTOR BASED IMAGING

(75) Inventors: Dror Shemesh, Petah Tikva (IL); Pavel Adamec, Haar (DE)

(73) Assignee: Applied Materials Israel, Ltd., Rehovot (IL)

(*) Notice: Subject to any disclaimer, the term of this patent is extended or adjusted under 35 U.S.C. 154(b) by 210 days.

(21) Appl. No.: 10/502,104

(22) PCT Filed: Oct. 22, 2003

(86) PCT No.: PCT/US03/33648

§ 371 (c)(1),
(2), (4) Date: Sep. 19, 2005

(87) PCT Pub. No.: WO01/45136

PCT Pub. Date: Jun. 21, 2001

(65) Prior Publication Data

US 2006/0054814 A1    Mar. 16, 2006

Related U.S. Application Data

(60) Provisional application No. 60/491,618, filed on Jul. 30, 2003.

(51) Int. Cl.
*H01J 37/244*    (2006.01)
(52) U.S. Cl. .................. 250/397; 250/307; 250/310
(58) Field of Classification Search .................. 250/397
See application file for complete search history.

(56) References Cited

U.S. PATENT DOCUMENTS

| | | | |
|---|---|---|---|
| 3,849,659 A | | 11/1974 | O'Keeffe |
| 4,321,510 A | | 3/1982 | Takigawa |
| 4,896,036 A | | 1/1990 | Rose et al. |
| 4,926,054 A | | 5/1990 | Frosien |
| 5,329,125 A | | 7/1994 | Feuerbaum |
| 5,481,109 A | * | 1/1996 | Ninomiya et al. ........... 250/310 |
| 5,627,373 A | | 5/1997 | Keese |
| 5,659,172 A | | 8/1997 | Wagner et al. |

(Continued)

FOREIGN PATENT DOCUMENTS

EP    1 045 426 A2    10/2000

(Continued)

OTHER PUBLICATIONS

Applied Materials, Inc., PCT/US03/14974 filed May 12, 2003, International Search Report, Jan. 27, 2004, ISA-EP, 6pp.

(Continued)

*Primary Examiner*—Phillip A Johnston
(74) *Attorney, Agent, or Firm*—SNR Denton US LLP

(57) ABSTRACT

A system and method for multi detector detection of electrons, the method includes the steps of directing a primary electron beam, through a column, to interact with an inspected object, directing, by introducing a substantial electrostatic field, electrons reflected or scattered from the inspected objects towards multiple interior detectors, whereas at least some of the directed electrons are reflected or scattered at small angle in relation to the inspected object; and receiving detection signals from at least one interior detector.

16 Claims, 7 Drawing Sheets

U.S. PATENT DOCUMENTS

| | | | |
|---|---|---|---|
| 5,734,164 A | 3/1998 | Sanford | |
| 5,894,124 A | 4/1999 | Iwabuchi et al. | |
| 5,895,917 A | 4/1999 | Ueda et al. | |
| 5,900,629 A | 5/1999 | Todokoro et al. | |
| 5,939,720 A * | 8/1999 | Todokoro | 250/310 |
| 5,952,667 A | 9/1999 | Shimizu | |
| 6,037,589 A | 3/2000 | Yonezawa et al. | |
| 6,064,486 A | 5/2000 | Chen et al. | |
| 6,066,853 A | 5/2000 | Nakasuji | |
| 6,084,238 A * | 7/2000 | Todokoro et al. | 250/310 |
| 6,172,365 B1 | 1/2001 | Hiroi et al. | |
| 6,184,526 B1 | 2/2001 | Kohama et al. | |
| 6,194,729 B1 | 2/2001 | Weimer | |
| 6,232,601 B1 | 5/2001 | Schmitt et al. | |
| 6,353,222 B1 | 3/2002 | Dotan | |
| 6,365,897 B1 | 4/2002 | Hamashima et al. | |
| 6,407,388 B1 | 6/2002 | Frosien | |
| 6,407,396 B1 | 6/2002 | Mih et al. | |
| 6,452,175 B1 | 9/2002 | Adamec | |
| 6,463,184 B1 | 10/2002 | Gould et al. | |
| 6,489,068 B1 | 12/2002 | Kye | |
| 6,498,068 B1 | 12/2002 | Ueda et al. | |
| 6,501,077 B1 | 12/2002 | Sawahata et al. | |
| 6,555,819 B1 | 4/2003 | Suzuki et al. | |
| 6,589,385 B2 | 7/2003 | Minami et al. | |
| 6,590,210 B1 | 7/2003 | Essers | |
| 6,635,873 B1 * | 10/2003 | Todokoro et al. | 250/310 |
| 6,646,262 B1 | 11/2003 | Todokoro et al. | |
| 6,674,075 B2 | 1/2004 | Petrov et al. | |
| 6,730,907 B1 * | 5/2004 | Feuerbaum et al. | 850/9 |
| 6,778,275 B2 | 8/2004 | Bowes | |
| 6,787,772 B2 * | 9/2004 | Ose et al. | 250/310 |
| 6,897,442 B2 | 5/2005 | Petrov | |
| 7,045,781 B2 * | 5/2006 | Adamec et al. | 250/310 |
| 7,223,974 B2 | 5/2007 | Petrov et al. | |
| 2001/0010362 A1 | 8/2001 | Simizu | |
| 2002/0179851 A1 | 12/2002 | Sato et al. | |
| 2002/0185599 A1 | 12/2002 | Kimura et al. | |
| 2003/0116717 A1 | 6/2003 | Knippelmeyer | |
| 2003/0205678 A1 | 11/2003 | Notte, IV | |

FOREIGN PATENT DOCUMENTS

| | | |
|---|---|---|
| EP | 1 263 018 A | 12/2002 |
| JP | 09-171791 | 6/1997 |
| JP | 2000 156189 A | 6/2000 |
| KR | 1998-081497 | 11/1998 |
| WO | 99/26272 | 5/1999 |
| WO | 99/46797 | 9/1999 |
| WO | 01/45136 A1 | 6/2001 |
| WO | 02/37523 A2 | 5/2002 |

OTHER PUBLICATIONS

Applied Materials Israel, Ltd.; CN Application No. 2003801104084 filed Oct. 22, 2003, Office Action dated Mar. 6, 2009, 5pp.

Applied Materials Israel, Ltd.; CN Application No. 2003801104084 filed Oct. 22, 2003, Office Action dated Feb. 5, 2010, 3pp.

Applied Materials Israel, Ltd.; JP Application No. 2005-507924 filed Oct. 22, 2003, Office Action dated Sep. 15, 2009, 4pp.

Applied Materials Israel, Ltd.: PCT/US2004/012468 Filed Apr. 22, 2004; International Search Report and Written Opinion; ISA/EP; Oct. 29, 2004; 16pp.

Applied Materials Israel, Ltd.: PCT/US2004/012468 Filed Apr. 22, 2004; International Preliminary Report on Patentability; International Bureau of WIPO; Nov. 10, 2005; 10pp.

Frosien J., et al.; "Compound Magnetic and Electrostatic Lenses for Low-Voltage Applications"; Journal of Vacuum Science and Technology: Part B, American Institute of Physics. New York, US, vol. 7, No. 6, Nov. 1, 1989, pp. 1874-1877.

Applied Materials Israel, Ltd.: PCT/US2003/015018 Filed May 12, 2003; International Search Report; ISA/EP; Jan. 26, 2004; 9pp.

Patent Abstracts of Japan, Oct. 12, 2001, JP 2001283759 1pg.

Patent Abstracts of Japan, vol. 1999, No. 11, Sep. 30, 1999, JP 11 162384 1pg.

Patent Abstracts of Japan, vol. 01, No. 385 (P-1094), Aug. 20, 1990—& JP 02 145947 A (Shimadzu Corp), Jun. 5, 1990, abstract; figure 1.

United States Patent Application entitled: A Focusing Assembly and Method for a Charged Particle Beam Column.

Patent Abstracts of Japan, vol. 1998, No. 13, Nov. 30, 1998—& JP 10 214586 A (Horon: KK), Aug. 11, 1998, abstract; figures 1, 2.

Applied Materials Israel, Ltd.; Korean Application No. 10-2006-7001930, Office Action dated Jul. 28, 2010, 6pp.

* cited by examiner

SCANNING ELECTRON MICROSCOPE HAVING MULTIPLE DETECTORS AND A METHOD FOR MULTIPLE DETECTOR BASED IMAGING

RELATED APPLICATION

The present patent application is a non-provisional application of International Application No. PCT/US03/33648, filed Oct. 22, 2003, which claims priority from U.S. Provisional Application 60/491,618 filed Jul. 30, 2003, which is herein incorporated by reference.

FIELD OF THE INVENTION

The invention relates to scanning electron microscopes and especially to a multiple-detector SEM and a method for multiple detector based detection.

BACKGROUND OF THE INVENTION

A prior art multi perspective scanning microscope (MPSI) system 10 is described in FIG. 1. System 10 includes an electron gun (not shown) for generating a primary electron beam, as well as multiple control and voltage supply units (not shown), an objective lens 12, in-lens detector 14 and external detectors 16. System 10 also includes deflection coils and a processor (not shown).

In system 10 the primary electron beam is directed through an aperture 18 within the in-lens detector 14 to be focused by the objective lens 12 onto an inspected wafer 20. The primary electron beam interacts with wafer 20 and as a result various types of electrons, such as secondary electrons, back-scattered electrons, Auger electrons and X-ray quanta are reflected or scattered. Secondary electrons can be collected easily and most SEMs mainly detect these secondary electrons.

System 10 is capable of detecting some of the emitted secondary electrons by in-lens detector 14 and by external detectors 16.

Objective lens 12 includes an electrostatic lens and a magnetic lens that introduce an electrostatic field and a magnetic field that leak from the lens towards the wafer. The collection of secondary electrons is highly responsive to the leaked electrostatic field while it hardly influenced by the leaked magnetic field.

The leaked electrostatic field attracts low energy secondary electrons and very low energy secondary electrons into the column. A significant part of the very low energy secondary electrons are directed through the aperture of in-lens detector 14 and are not detected. Low energy secondary electrons are directed towards the in-lens detector 14. High-energy secondary electrons are detected if their initial trajectory is aimed towards one of the detectors. Very low energy is typically below 2 eV, while low energy typically ranges between 2 eV and 15 eV.

In practice, when the working distance (between the column lower end and the wafer) is decreased (for example, below 0.5 mm), or when the cap voltage (the voltage that is applied to a lower portion of the electrostatic lens) is increased (for example, above 1 kV), most of the secondary electrons are not detected at all. They will enter the aperture of the In-lens detector 14. Such a decrement (in working distance) and/or increment (in voltage cap) also direct less secondary electrons to be directed towards the external detector, and vise versa.

Effective defect review tool requires both types of detectors in order to capture all types of defects. In-lens detector 14 is usually used for determining a contrast between different materials, and is also useful in voltage contract mode as well as in HAR mode. The In-lens detector 14 is also very sensitive to pattern edges. External detectors 16 are much more sensitive to the topography of the wafer. They external detectors are also less susceptible to wafer charging, which is significant when imaging highly resistive layers.

The working distance and the cap voltage also influence the resolution of the system. A decrease in the working distances reduces the chromatic aberration thus improving resolution, and vice verse.

As illustrated above if the working distance is decreased the resolution improves but the amount of detected electrons decrease.

There is a need to provide a system and method that allows both high-resolution and multi perspective capabilities.

U.S Pat. No. 6,555,819 of Suzuki et al (which is incorporated herein by reference) describes a multi-detector SEM having magnetic leakage type objective lens where the magnetic field largely influences the trajectory of emitted secondary electrons. This SEM has various disadvantages, such as not being capable of providing tilted images. Suzuki has a reflector that includes an aperture through which the primary electron beam passes, thus reflected electrons may pass through this aperture and remain un-detected.

SUMMARY OF THE INVENTION

The invention provides a system and method for high-resolution multi-perspective SEM imaging that also provides high quality tilt images, including relatively high tilt angles that involve mechanical tilt.

The invention provides a system and method for high-resolution multi-perspective SEM detection of high aspect ratio holes (HAR mode).

The invention provides a system that includes multiple detectors that define multiple collection zones, some being associated with different angular regions.

The invention allows optimizing the system parameters for allowing improved in-lens detection as well as improved central lens detection. The parameters (such as cap voltage, wafer voltage, working distance) can determine the relationship between the SNR (signal to noise ratio) of each detector.

The invention provides a method for multi detector detection of electrons, the method includes the steps of: (i) directing a primary electron beam, through a column, to interact with an inspected object; (ii) directing, by introducing a substantial electrostatic field, electrons reflected or scattered from the inspected objects towards multiple interior detectors, whereas at least some of the directed electrons are reflected or scattered at small angle in relation to the inspected object; and (iii) receiving detection signals from at least one interior detector.

The invention provides a system for multi detector detection of electrons, the system includes multiple interior detectors for providing detection signals, a column through which electrons may propagate, and means for directing a primary electron bearn, through the column, to interact with an inspected object and for directing, by introducing a substantial electrostatic field, electrons reflected or scattered from the inspected objects towards the multiple interior detectors, whereas at least some of the directed electrons are reflected or scattered at small angle in relation to the inspected object.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
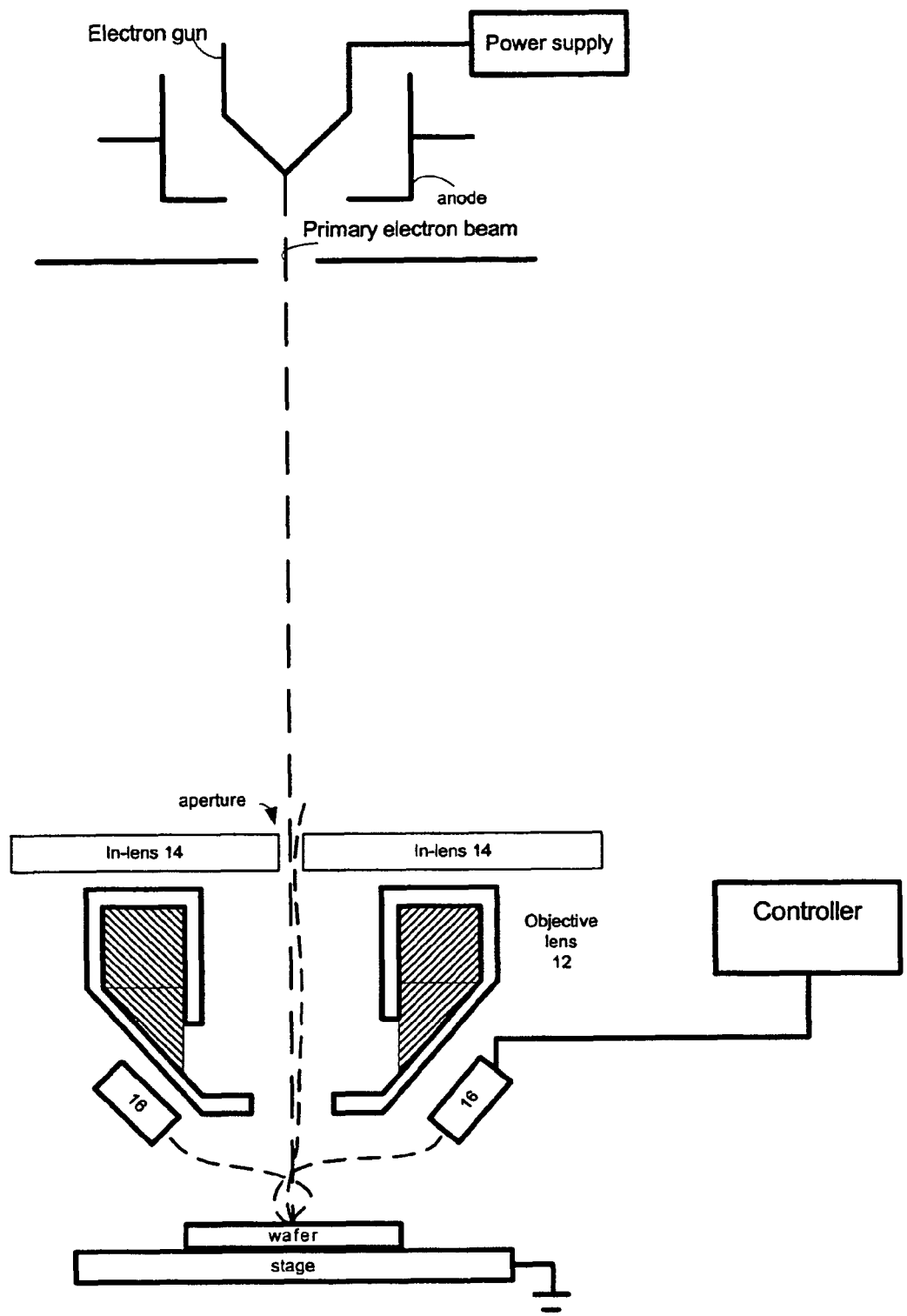
FIG. 1 describes a portion of a prior art Scanning Electron Microscope.
Figure 2:
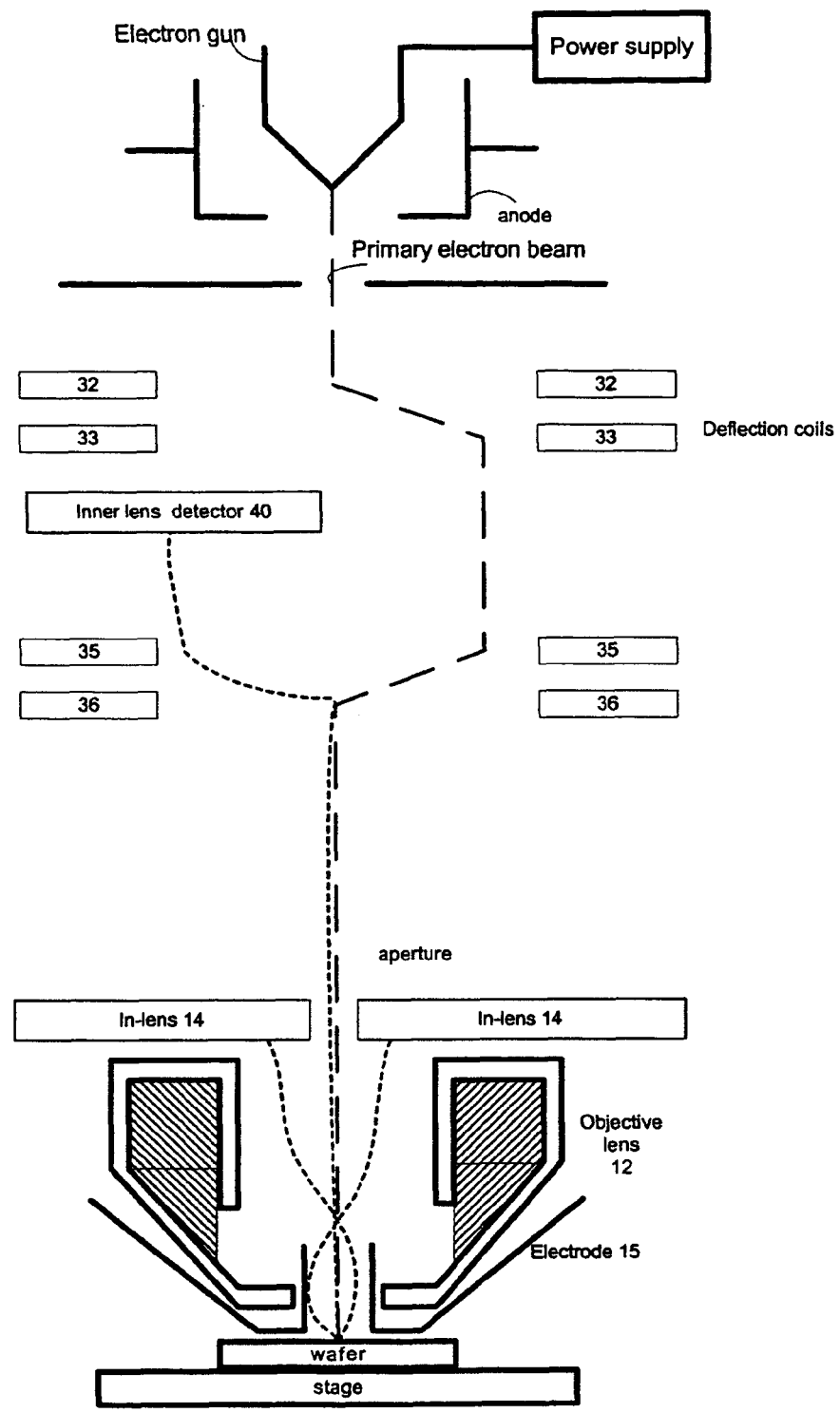
FIG. 2 illustrates a portion of a SEM according to an embodiment of the invention.

FIG. 2 is an illustration of a portion of multiple detector SEM in accordance to an embodiment of the invention. FIG. 2 also illustrates an exemplary path of a primary electron beam path, as well as the paths of electrons that are scattered or reflected from an inspected object, such as but not limited to a wafer or a reticle.

The primary electron beam propagates along an optical axis and is than (i) tilted at a first direction, (ii) tilted at an opposite direction such as to propagate along a secondary optical axis that is parallel to the optical axis but spaced apart from the optical axis, (iii) tilted, at a second direction, towards the optical axis and then (iv) tilted, at a direction opposing the second direction, such as to propagate along the optical axis. The mentioned above tilt operations may be generated by magnetic deflection coils 32-36. A system and method for double tilt is described at patent application Ser. No. 10/146,218 filed 13 May 2002, and is incorporated herein by reference.

It is noted that other tilt schemes may be implemented, such as performing only the fist two tilts, such that the primary electron beam interacts with the inspected object while propagating along the secondary axis.

The in-lens detector is located at the final part of the propagation path, where the primary electron beam propagates along the optical axis. The in-lens detector has an aperture that is positioned such as to surround the optical axis.

Once electrons are emitted/scattered as a ressult as an interaction between the primary beam and the inspected object, they are attracted, due to a strong electrostatic field, towards the in-lens detector and to the aperture of that detector. The strength of the electrostatic field determines which secondary electrons are attracted to the in-lens detector and which are attracted to the aperture of the in-lens detector.

Secondary electrons that propagate through the aperture of in-lens detector 14 are eventually tilted at a second direction towards an inner-lens detector 40.

This configuration enables to receive information from high aspect ratio (HAR) hole. When applying a strong electrostatic field electrons that interact with the bottom of such a HAR hole or even the lower parts of that hole sidewalls are attracted to propagate through the aperture towards the inner-lens detector.

By using a conical shaped objective lens and high electrostatic fields the system enables tilted views. The inspected object and/or SEM column can also be mechanically tilted.

By modifying the cap voltage and/or the working distance, it is possible to determine how to divide the electrons between in-lens detector 14 and the inner-lens detector 40. In this way, it is possible to vary the signal to noise ratio of both detectors in order to get an optimum between signal to noise and directional information from the sample. For example, a decrease in the cap voltage can increase the signal in the Inner-lens detector, decrease the topographical information from the inner-lens detector and decrease the visibility of HAR information.

By applying a relatively strong electrostatic field the inner lens detector detects electrons that were one either not detected (passed through the aperture) or detected by the in-lens detector, while the in-lens detector detects electrons that once were detected by the external detectors.

The inventors applied a cap voltage of 500 V, at a working distance of 1.4 mm, with an in-lens aperture of 2 mm diameter and detected at the in-lens detector, electrons that were used to be detected by prior art external detectors.

According to another aspect of the invention the multi-detector SEM may include multiple in-lens and inner-lens detectors, each for collecting electrons from a certain collection zone. As the collection zones differ from each, such a configuration can provide additional directional information. The collection zones may partially overlap and some of the detectors may be positioned above each other.

A ring shaped scintilator may be used for each of said in-lens and/or inner lens detector. The ring may be divided to slices, for increasing the amount of directional information.

Figure 3:
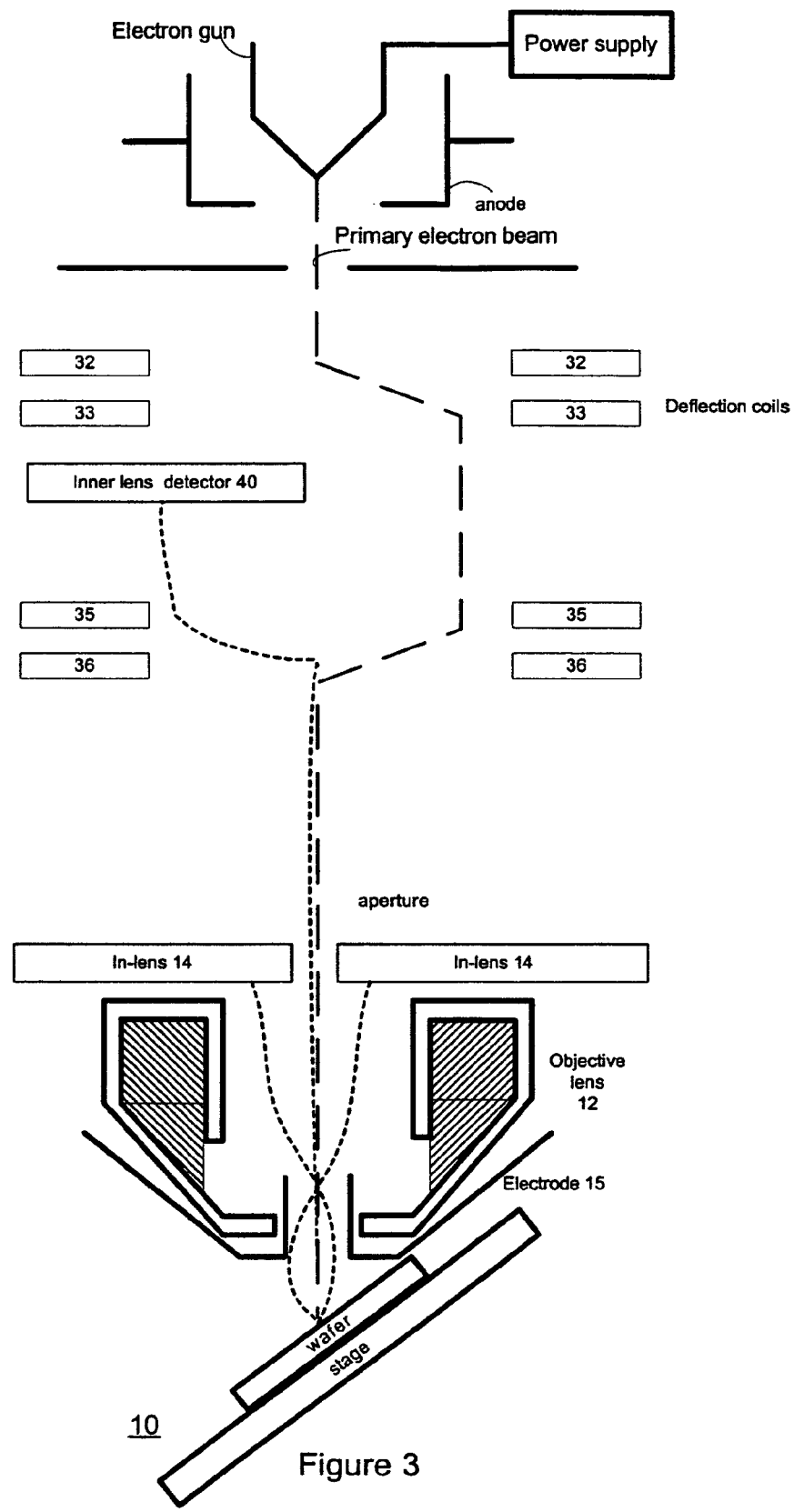
FIG. 3 illustrates a portion of a SEM according to an embodiment of the invention, where a tilt is introduced between an inspected object and the SEM.

As illustrated by FIG. 3 the system is also capable of multi-perspective detection even when a tilt is introduced between the electron beam and the inspected object. To achieve a large tilt angle a mechanical tilt or a combination of electrical and mechanical tilt is required A method for combining mechanical as well as electrical tilt is described at U.S. patent application Ser. No. 10/154,530 titled "charged particle beam column and a method for directing a charged particle beam", filed 22 May 2002, which is incorporated herein by reference.

Figure 4A:
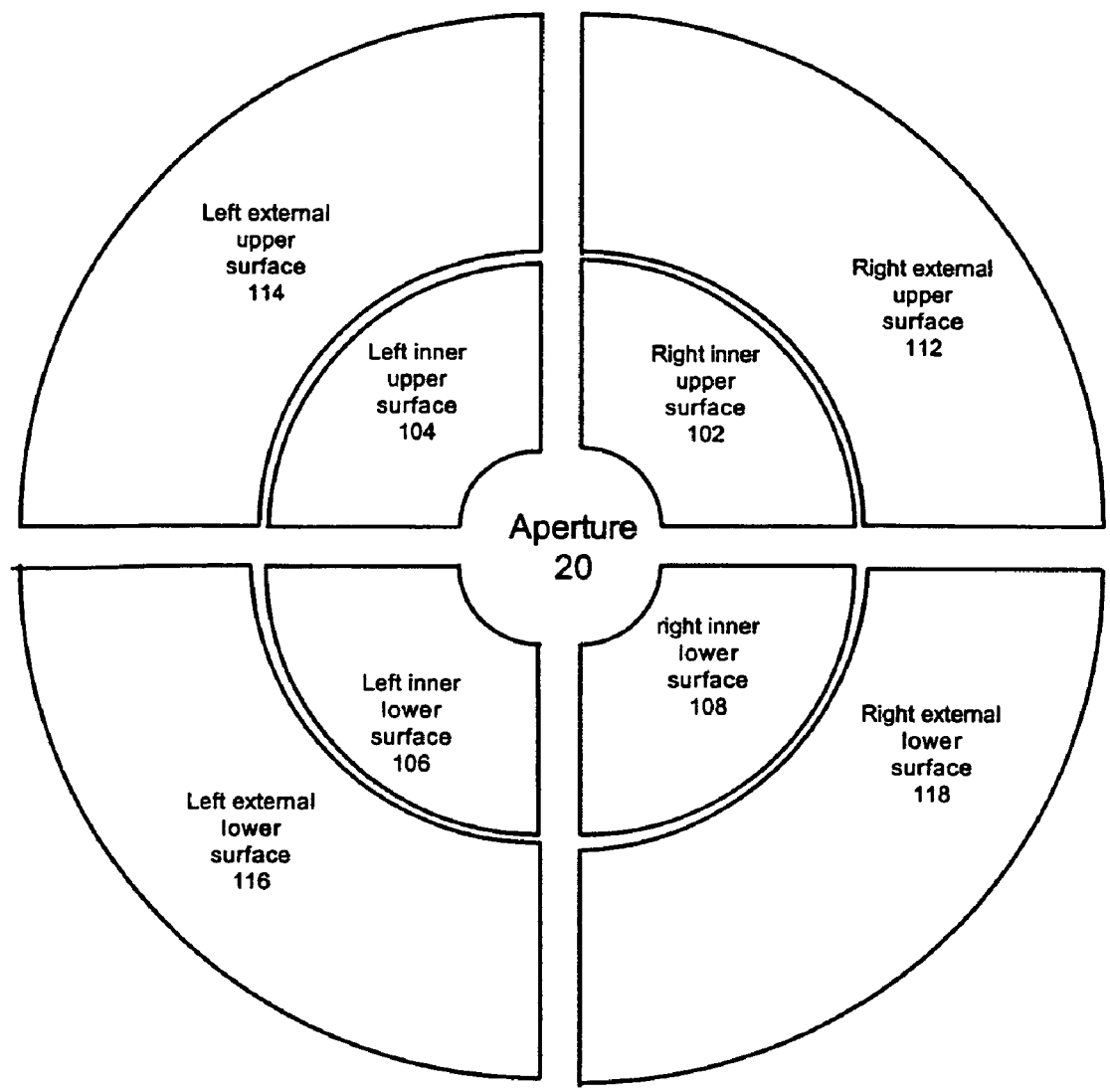
FIGS. 4a-4c illustrate various configurations of detectors and especially detection surfaces of these detectors, in accordance to embodiments of the invention.
Figure 4B:
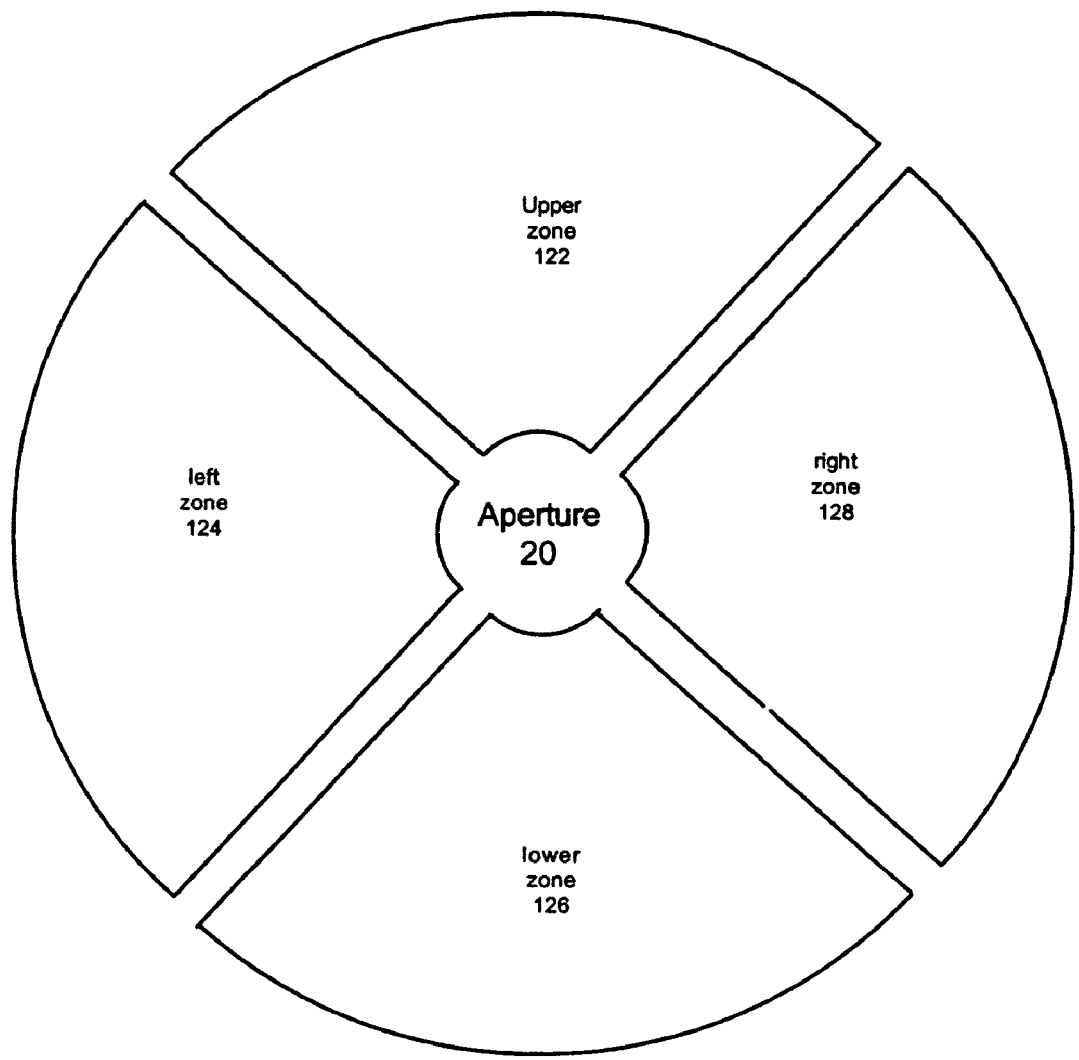

FIGS. 4a-4b describe various configurations of in-lens and inner lens detector detection surfaces that define multiple detection surfaces. FIG. 4a illustrates an in-lens detector 14 that includes eight detection surfaces: right inner upper surface 102, left inner upper surface 104, left inner lower surface 106 and right inner lower surface 108, that form an inner circular shaped zone that circles aperture 20, as well as right external upper surface 112, left external upper surface 114, left external lower surface 116 and right external lower surface 118, that form an ring shaped zone that surrounds the four inner collection surfaces.

Each surface defines a collection zone that also depends upon the location of the detector within the column and also is responsive to an electrostatic field that is applied by the objective lens.

FIG. 4b illustrates an in-lens detector that includes four collection surfaces, that are rotated at 45 degrees in relation to the collection surfaces of FIG. 4a. The collection surfaces include upper surface 122, left surface 124, lower surface 126 and right surface 128.

Figure 4C:
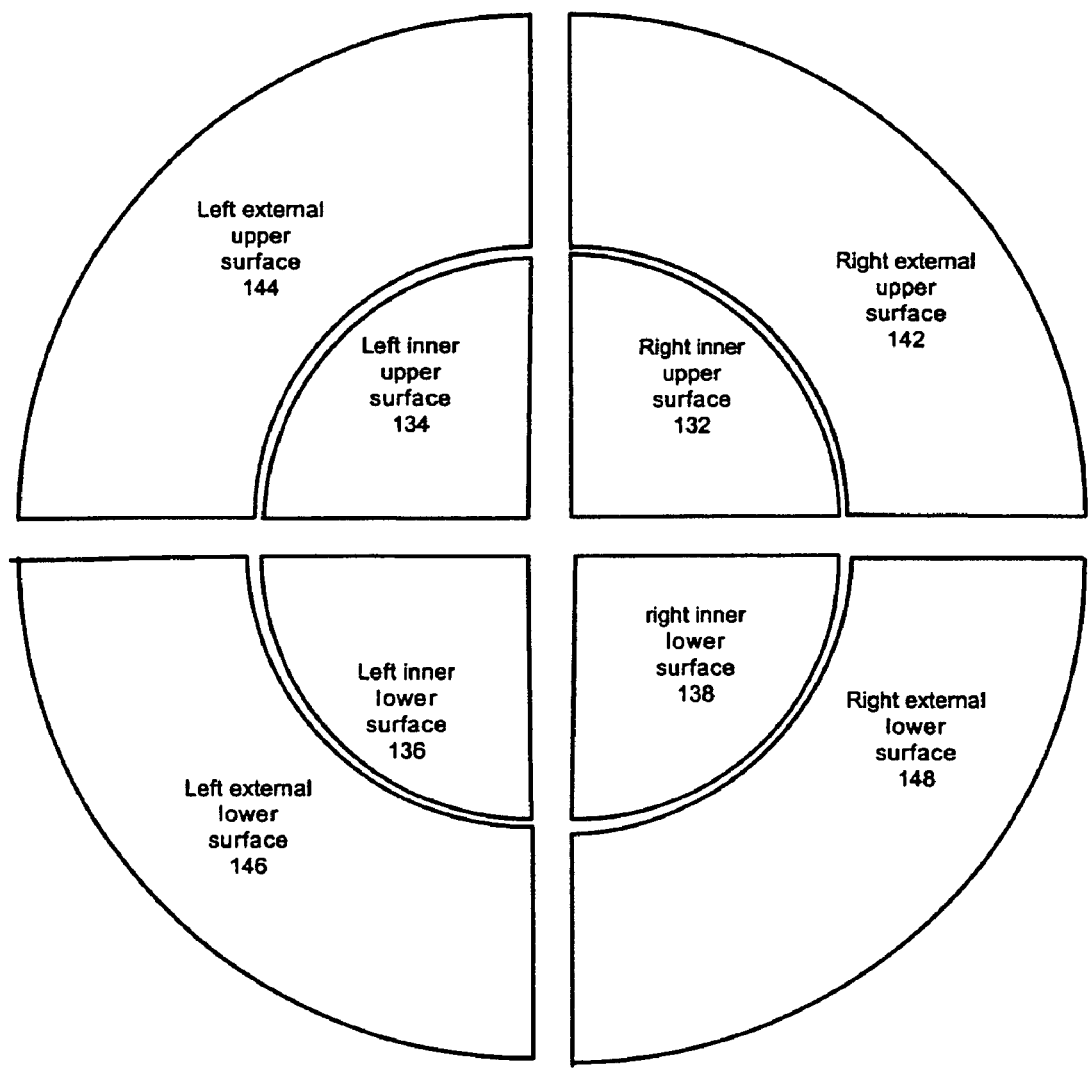

FIG. 4c illustrates an inner-lens detector that includes eight detection surfaces: right inner upper surface 132, left inner upper surface 134, left inner lower surface 136 and right inner lower surface 138, that form an inner circular shaped zone, as well as right external upper surface 142, left external upper surface 144, left external lower surface 146 and right external lower surface 148, that form an ring shaped zone that surrounds the four inner collection surfaces. The inner zone of inner lens does not surround an aperture, thus even electrons that are directed at a very small angle in relation to the optical axis are detected.

The invention the electrostatic field can be introduced by multiple electrodes of various shapes and arrangements. Some of the embodiments are illustrated at U.S. patent application Ser. No. 10/423,289 titled "objective lens arrangement for use in a charged particle beam column", that is incorporated herein by reference. Briefly, the mentioned patent application describes an objective lens that has an electrostatic lens that includes upper and lower electrodes arranged in a spaced apart coaxial relationship along an optical axis of the lens arrangement.

The system may use detection signals received from the in lens detector and inner lens detectors in various manners. It can process detection from each detector independently, and can determine the presence of a defect and/or generate SEM images in response to detection signals from one or more detector.

There are various prior art methods for processing detection signals from multiple detectors, one being illustrated at U.S. Pat. No. 5,659,172 of Wagner that is incorporated herein by reference.

Figure 5:
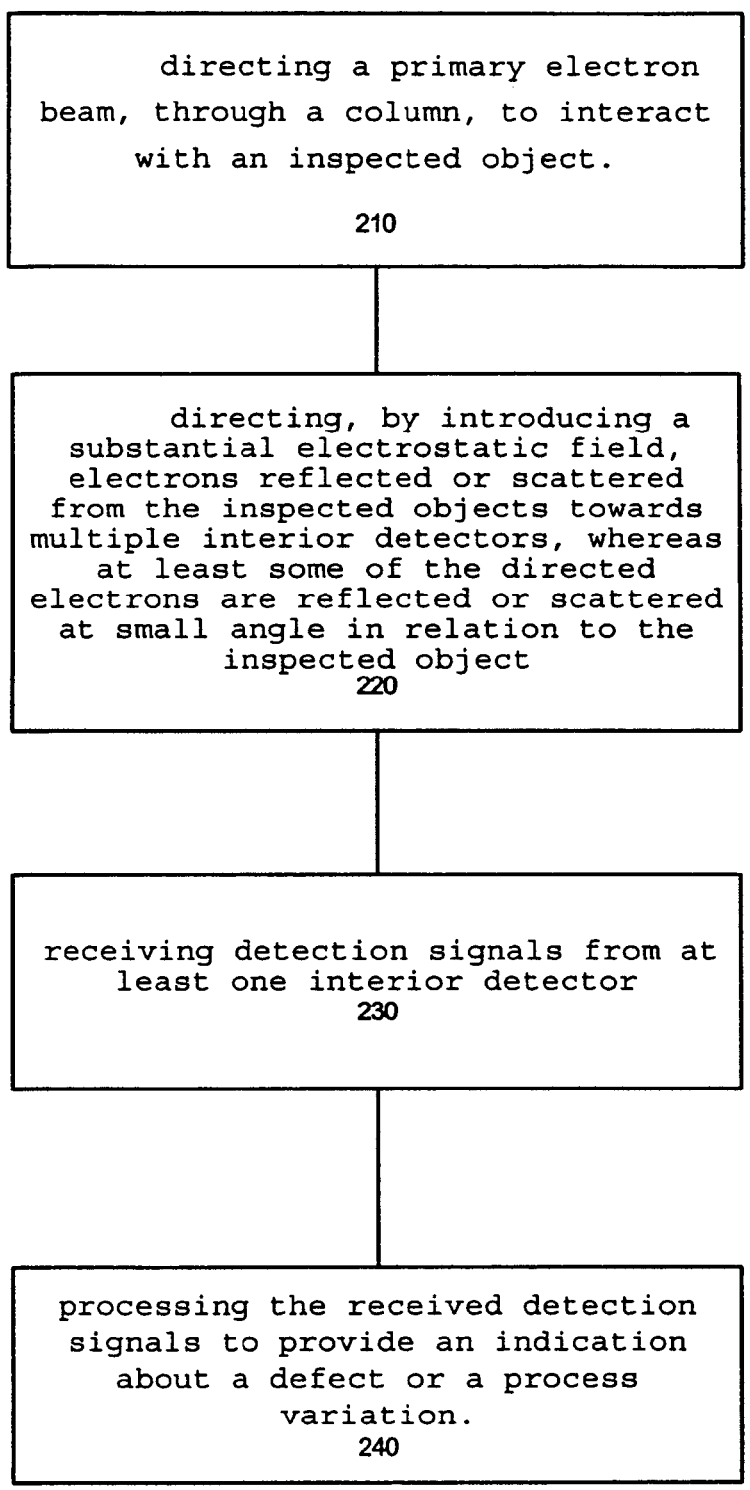
FIG. 5 is a flow chart illustrating a method for inspecting an object, according to an embodiment of the invention.

FIG. 5 is a flow chart of method 200 for multi detector detection of electrons, in accordance with an embodiment of the invention. Method 200 starts at step 210 of directing a primary electron beam, through a column, to interact with an inspected object. Step 210 is followed by step 220 of directing, by introducing a substantial electrostatic field, electrons reflected or scattered from the inspected objects towards multiple interior detectors, whereas at least some of the directed electrons are reflected or scattered at small angle in relation to the inspected object. Step 220 is followed by step 230 of receiving detection signals from at least one interior detector.

It is noted that the primary electron beam as well as scattered or reflected electrons can be manipulated by the same units, and that usually steps 210 and 220 occur almost at the same time.

Step 220 may involve introducing a substantial electrostatic field by various manners. For example, it may involve introducing a first voltage potential difference between the inspected object and a first portion of the column while and introducing a second voltage potential difference between a second portion of the column and the inspected object. The first portion is usually positioned below the second portion and the first voltage potential difference is smaller than the second voltage potential difference. Conveniently, the first portion is an anode that is positioned above the magnetic lens, while the second portion is positioned below the top of the magnetic lens or even below the magnetic lens. The lower edge of the second portion may define the working distance between the SEM and the inspected object.

Step 210 may include at least one tilt of the primary electron beam. This tilt may be forced by deflection units that may also deflect electrons that are scattered or reflected from the inspected object. Step 210 may include directing the primary electron beam to propagate along an optical axis; tilting the primary electron beam away from the optical axis; and tilting the primary electron beam such as to propagate along a secondary optical axis that is parallel to the optical axis but spaced apart from the optical axis. Step 210 may also include tilting the electron beam such as to propagate towards the optical axis and tilting the primary electron beam such as to propagate along the optical axis.

Step 220 may involve positioning the inspected area of the inspected object within the substantial electrostatic lens.

Method 200 can be implemented at various tilt states. Whereas a tilt state is characterized by the tilt angle (that can range between about very small angles to angles that are slightly smaller than 90 degrees) between the primary electron beam and the inspected area.

Method 200 can include additional steps such as step 240 of processing the received detection signals to provide an indication about a defect or a process variation.

It is further noted that method 200 may include a step of defining/altering collection zones by applying different voltage values to the electrostatic lens. This may result in optimizing the system parameters for allowing optimal performances (in terms of resolution, aberrations and the like) of the in-lens and/or the inner-lens detectors.

The present invention can be practiced by employing conventional tools, methodology and components. Accordingly, the details of such tools, component and methodology are not set forth herein in detail. In the previous descriptions, numerous specific details are set forth, such as shapes of cross sections of typical lines, amount of deflection units, etc., in order to provide a thorough understanding of the present invention. However, it should be recognized that the present invention might be practiced without resorting to the details specifically set forth.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

We claim:

1. A method comprising the steps of:
   directing a primary election beam to propagate along an optical axis through a column;
   deflecting the primary electron beam away from the optical axis upstream of an inner lens detector and back to propagating along the optical axis downstream of the inner lens detector, so that the primary electron beam propagates around the inner lens detector, said upstream and downstream locations each defined with respect to a direction of a propagation of the primary electron beam;
   impinging the primary electron beam on an object, thereby producing both low-energy and high-energy electrons resulting from at least one of reflection and scattering of the primary electron beam from the object, each of the produced low-energy and high-energy electrons having an initial trajectory with respect to the object;
   detecting a first portion of the produced high-energy electrons by an in-lens detector;
   directing, by introducing a substantial electrostatic field, a trajectory of the produced low-energy electrons and a second portion of the produced high-energy electrons towards the inner lens detector, wherein the initial trajectory of the second portion of the produced high-energy electrons is substantially coincident with the optical axis;
   detecting the directed low-energy electrons and the second portion of high-energy electrons by the inner lens detector; and
   controlling a division of the low-energy and high-energy electrons between the in-lens detector and the inner lens detector by modifying the substantial electrostatic field and modifying a distance between the column and the object.

2. The method of claim 1 wherein introducing a substantial electrostatic field comprises introducing a first voltage potential difference between the object and a first portion of the column and introducing a second voltage potential difference between a second portion of the column and the object.

3. The method of claim 2 wherein the first portion of the column is positioned below the second portion and wherein the first voltage potential difference is smaller than the second voltage potential difference.

4. The method of claim 1 further comprising:
receiving detection signals corresponding to at least one of the low-energy electrons, the first portion of high-energy electrons, and the second portion of high-energy electrons; and
processing the received detection signals to provide an indication about a defect or a process variation.

5. The method of claim 1 further comprising a step of varying the substantial electrostatic field to alter one or more collection zones of the in-lens and inner lens detectors.

6. The method of claim 1 wherein an inspected area of the object is positioned within the substantial electrostatic field.

7. The method of claim 6 wherein the primary electron beam impinges on the inspected area at a tilt angle.

8. The method of claim 7 wherein the tilt angle ranges between acute angles and obtuse angles.

9. The method of claim 1 wherein detected electrons include electrons from a lower portion of a high aspect ratio hole.

10. A system comprising:
means for directing a primary electron beam to propagate along an optical axis through a column;
means for deflecting the primary electron beam away from the optical axis upstream of an inner lens detector and back to propagating along the optical axis downstream of the inner lens detector, so that the primary electron beam propagates around the inner lens detector, said upstream and downstream locations each defined with respect to a direction of a propagation of the primary electron beam;
means for impinging the primary electron beam on an object, thereby producing both high-energy and low-energy electrons resulting from at least one of reflection and scattering of the primary electron beam from the object, each of the produced high-energy and low-energy electrons having an initial trajectory with respect to the object;
an in-lens detector configured to detect a first portion of the produced high-energy electrons;
means for directing, by the introduction of a substantial electrostatic field, a trajectory of the produced low-energy electrons and a second portion of the produced high-energy electrons towards the inner lens detector, wherein the initial trajectory of the second portion of the produced high-energy electrons is substantially coincident with the optical axis;
the inner lens detector configured to detect the directed low-energy electrons and the second portion of high-energy electrons; and
means for controlling a division of the low-energy and high-energy electrons between the in-lens detector and the inner lens detector by modifying the substantial electrostatic field and modifying a distance between the column and the object.

11. The system of claim 10 wherein the column comprises a first portion that is associated with a first voltage level and a second portion that is associated with a second voltage level.

12. The system of claim 11 wherein the first portion of the column is positioned below the second portion.

13. The system of claim 10 further adapted to vary the substantial electrostatic field to alter one or more collection zones of the in-lens and inner lens detectors.

14. The system of claim 10 wherein an inspected area of the object is positioned within the substantial electrostatic field.

15. The system of claim 14 further capable of introducing a tilt between the primary electron beam and the inspected area.

16. The system of claim 10 wherein the produced electrons include electrons from a lower portion of a high aspect ratio hole.

* * * * *

UNITED STATES PATENT AND TRADEMARK OFFICE
CERTIFICATE OF CORRECTION

| | | |
|---|---|---|
| PATENT NO. | : 7,847,267 B2 | Page 1 of 1 |
| APPLICATION NO. | : 10/502104 | |
| DATED | : December 7, 2010 | |
| INVENTOR(S) | : Dror Shemesh and Pavel Adamec | |

It is certified that error appears in the above-identified patent and that said Letters Patent is hereby corrected as shown below:

TITLE PG, ITEM (87) PCT Pub. No. section:

"WO01/45136" should read -- WO05/17511 --.

TITLE PG, ITEM (87) PCT Pub. Date section:

"Jun. 21, 2001" should read -- Feb. 24, 2005 --.

Signed and Sealed this
Thirteenth Day of September, 2011

David J. Kappos
*Director of the United States Patent and Trademark Office*